United States Patent [19]

Sanders et al.

[11] Patent Number: 4,471,656

[45] Date of Patent: Sep. 18, 1984

[54] APPARATUS FOR FLUID MASS MEASUREMENT

[75] Inventors: Paul J. Sanders, Concord; Robin A. Goguen, Fitchburg, both of Mass.

[73] Assignee: Oil Recovery Systems, Inc., Greenville, N.H.

[21] Appl. No.: 465,777

[22] Filed: Feb. 11, 1983

[51] Int. Cl.³ .............................................. G01F 23/00
[52] U.S. Cl. ...................... 73/438; 33/126.6; 73/290 R; 73/432 R; 364/509; 364/567
[58] Field of Search .............. 73/432 R, 454, 447, 73/432 G, 32 R, 438, 439, 290 R; 33/126.6, 126.5; 364/558, 581, 509, 564, 567

[56] References Cited

U.S. PATENT DOCUMENTS

| | | | |
|---|---|---|---|
| 2,669,123 | 2/1954 | Ballard | 73/454 |
| 2,921,469 | 1/1960 | Newton | 73/290 |
| 3,038,336 | 6/1962 | Peters | 73/299 |
| 3,184,965 | 5/1965 | Noik | 73/152 |
| 3,473,379 | 10/1969 | Stephens et al. | 73/301 |
| 3,623,366 | 11/1971 | Rowell | 73/301 |
| 3,772,915 | 11/1973 | Stamler | 364/558 |
| 4,193,303 | 3/1980 | Egnell | 73/438 |
| 4,365,509 | 12/1982 | Cornelis | 73/290 R |

*Primary Examiner*—S. Clement Swisher

[57] ABSTRACT

Apparatus for measuring the total mass of the fluid in a container, having pressure responsive, density determination means adapted to determine the localized density of the fluid as a function of pressure differential between two closely spaced, vertically separated measuring points in the fluid, means enabling the density determination means to determine the localized density values throughout the depth of the fluid, storage means for storing predetermined horizontal cross-sectional area values of the container as a function of depth, and computational circuitry responsive to the density determination means and the storage means for providing a total mass signal corresponding to the integral, over the depth of the fluid, of the product of localized density values times the corresponding area values.

11 Claims, 6 Drawing Figures

APPARATUS FOR FLUID MASS MEASUREMENT

BACKGROUND OF THE INVENTION

This invention relates to apparatus for measuring the mass of a fluid in a container, e.g., oil in a tank.

Storage, loading and delivery of large quantities of oil (and other liquids and powders) requires repeated determination of the mass of fluid being handled. In typical measuring devices, an element measures the temperatures at a number of regions in the container. Then the mass density in each region (corresponding to the temperature there) is multiplied times the volume of that region and the products are accumulated as the total mass. Fluid in such a tank typically includes a layer of water (e.g. water which has settled to the tank bottom), which affects the measurement of the total oil mass.

SUMMARY OF THE INVENTION

In general, the invention features apparatus for measuring the total mass of the fluid in a container, having pressure responsive, density determination means adapted to determine the localized density of the fluid as a function of pressure differential between two closely spaced, vertically separated measuring points in the fluid, means enabling the density determination means to determine the localized density values throughout the depth of the fluid, storage means for storing predetermined horizontal cross-sectional area values of the container as a function of depth, and computational circuitry responsive to the density determination means and the storage means for providing a total mass signal corresponding to the integral, over the depth of the fluid, of the product of localized density values times the corresponding area values.

In preferred embodiments, the density determination means includes a vertically movable pressure transducer and the means enabling determination of density values throughout the fluid depth includes traverse means for moving the transducer throughout the depth of the fluid, and a level indicator for providing values indicative of the vertical location of the transducer in the fluid with respect to each of its pressure readings; the pressure transducer has two pressure sensors at two vertically spaced-apart positions and is arranged to provide signals corresponding to the difference in pressures at the two positions, the signals being indicative of the mean localized density of the fluid in the region between the two positions; the apparatus is adapted for use with fluids whose density varies with temperature variations over the depth of the fluid and the computational circuitry is adapted to determine the integral in steps each corresponding to a finite interval of depth, and the finite interval and the vertical distance between the spaced-apart positions of the pressure sensors being selected to be small compared with the magnitude of variations, over the depth of the fluid, of the cross-sectional area and the density of the fluid; the container holds an additional fluid vertically separate from the fluid to be measured, the additional fluid having an electrical conductivity different from the fluid to be measured, and the apparatus includes an element sensitive to electrical conductivity, the apparatus responsive to the element to exclude the mass of the additional fluid from the total mass signal; the computational circuitry is adapted, on the basis of differences in electrical conductivity, to measure oil, and to exclude water; the storage means is adapted to store the cross-sectional area values for different containers having respectively different geometric configurations; the storage means is adapted to store the localized density values; the computational circuitry has programmable arithmetic processing means for computing the total mass signal, and signal flow control circuitry connected to route the localized density signals and the stored cross-sectional area values to the arithmetic processing means; the computational circuitry also has fluid sensing means for delivering immersion signals indicative of when the density determination means is not immersed within the fluid, the signal flow control circuitry is adapted to route the immersion signals to the arithmetic processing means, and the arithmetic processing means is arranged to limit the total mass signal computation to positions at which the density determination means is immersed in the fluid; and the apparatus includes an element sensitive to the electrical conductivity of the fluid in which the density determination means is immersed, the signal flow control circuitry is connected to route signals from the element to the arithmetic processing means, and the arithmetic processing is arranged to limit the total mass signal computation to positions at which the density determination means is immersed in the fluid to be measured.

The total mass is accurately and easily determined for a container of any configuration, without measuring temperature or requiring a priori knowledge of the dependence of density on temperature or depth the mean density in various regions is easily determined by the two sensors of the transducer; the mass of the measured fluid can be determined despite the presence of the additional fluid; and the mass measurement can be made easily for a variety of containers.

Other advantages and features will be apparent from the description of the preferred embodiments and from the claims.

DESCRIPTION OF THE PREFERRED EMBODIMENTS

We first briefly describe the drawings.

Drawings

Structure

Figure 1:
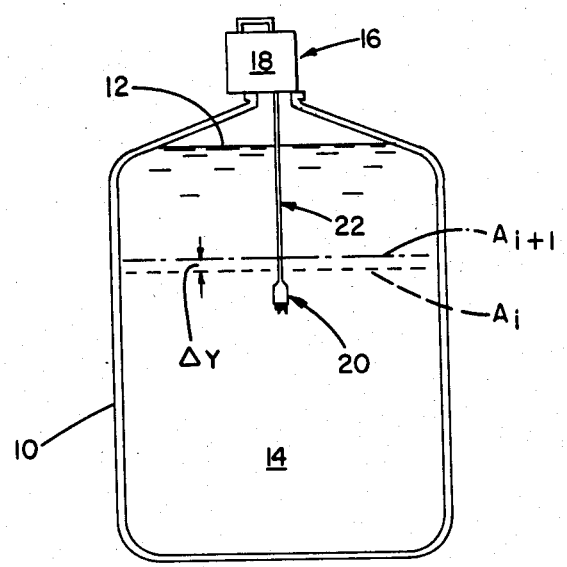
FIG. 1 is a sectional side view of a container of fluid showing a mass measuring station, gauging tape and transducer according to the invention.

Referring to FIG. 1, tank 10 is filled to level 12 with oil 14. Mass measuring system 16 includes measuring station 18 (positioned above the tank) and probe 20 suspended in the oil by gauging tape 22.

Figure 2:
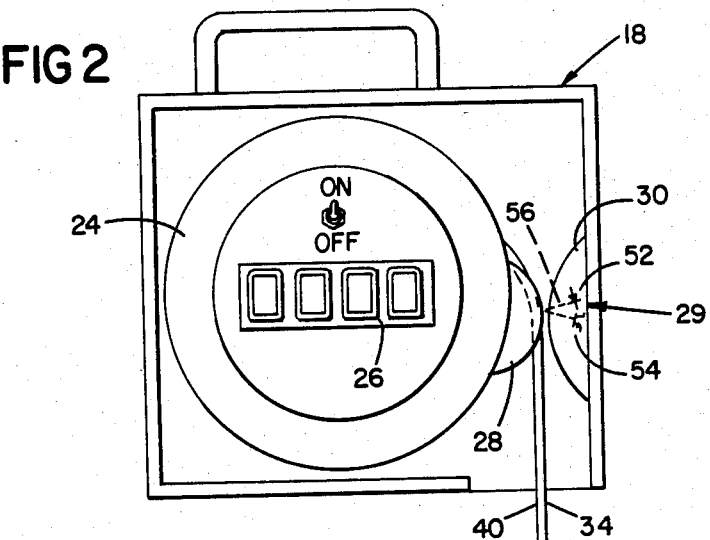
FIG. 2 is a side view of the mass measuring station, gauging tape and transducer of FIG. 1, with the cover of the measuring station removed.

Referring to FIG. 2, measuring station 18 has reel 24 for winding and unwinding tape 22 to raise and lower probe 20 in the tank. Tape 22 is wound and unwound over hub 28 so that the side 34 of tape 22 facing away from reel 24 is exposed to optical mark sensor 29 in housing 30.

Figure 3:
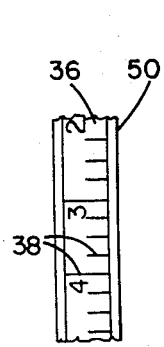
FIGS. 3 and 4 are views of opposite faces of a segment of the gauging tape of FIG. 1.
Figure 4:
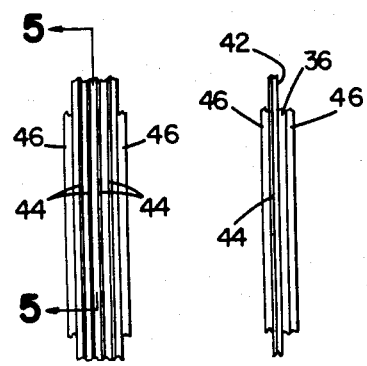
Figure 5:
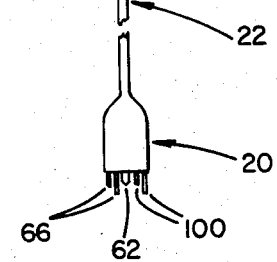
FIG. 5 is a sectional side view (at 5—5' in FIG. 4) of a segment of the gauging tape of FIGS. 3, 4.

Referring to FIGS. 3, 4, and 5, tape 22 has a supporting layer 36 (e.g., steel), side 34 of which is imprinted with periodic marks 38 (e.g., every ¼") in a color which contrasts with the surface of layer 36. The other side of layer 36 (i.e., side 40 in FIG. 2) is coated with insulating layer 42 (e.g., nylon or enamel) on which four silver electrical conductors 44 are silkscreened, brushed or extruded. Both sides of tape 22 are coated with abrasive-resistant and electrochemically-resistant insulating layers 46.

Referring again to FIG. 2, optical mark sensor (level indicator) 29 includes light emitting diode (LED) 52 and phototransistor 54, which are positioned (relative to each other and to side 34 of tape 22) so that light path 56 from the LED is reflected from the tape onto the phototransistor, causing a change in the phototransistor's output whenever a mark 38 is located at the point where light path 56 is being reflected.

Figure 6:
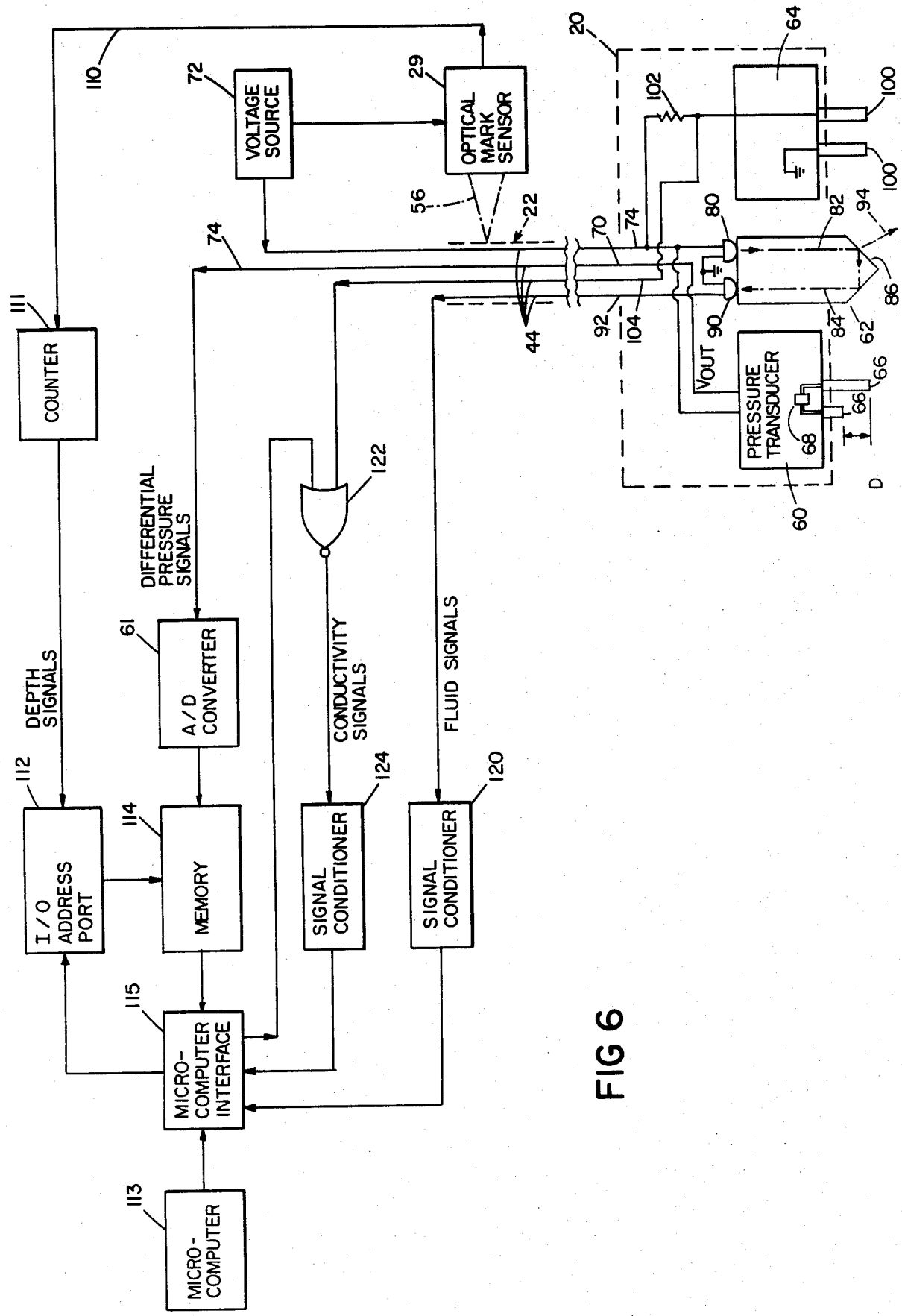
FIG. 6 is a block diagram of the circuitry of the measuring station and transducer of FIG. 1.

Referring to FIG. 6, probe 20 contains a differential pressure transducer 60, a fluid sensor 62, and a conductivity probe 64, all connected by wires 44 to measuring station 18.

Pressure transducer 60 has a pair of pressure ports 66 (vertically separated by a distance D). Pressure ports 66 are pneumatically connected by tubes to a pressure transducer element 68 (semiconductor, inductive or capacitive), which is sensitive to the difference in pressure (and hence to the mean density of the liquid) between ports 66. Element 68 is powered over line 70 from voltage source 72 (in the measuring station) and provides an analog output voltage indicative of the pressure differential over line 74 to an analog-to-digital converter 61 (in measuring station 18).

In fluid sensor 62, an infrared LED 80 (powered over line 70) projects infrared radiation along path 82 inside transparent light conductor 84. Surface 86 reflects the radiation back through conductor 84 to phototransistor 90 whenever fluid sensor 62 is in air (and hence the relative refractive indexes of the air and the conductor cause internal reflection in the conductor), and phototransistor 90 delivers a signal over line 92 indicating that the sensor is not in fluid. Whenever sensor 62 is in fluid, the relative refractive indexes at surface 86 permit the radiation to exit the conductor, along path 94, thereby interrupting the signal from phototransistor 90.

Conductivity sensor 64 has a pair of spaced-apart electrodes 100, one of which is grounded, and the other of which is connected (through dropping resistor 102 and line 70) to voltage source 72, and (directly through line 104) to measuring station 18. The current flowing through resistor 102 (and hence the voltage on line 104) depends on the conductivity of the fluid (e.g., water or oil) surrounding electrodes 100.

At the measuring station, the output of optical mark sensor 29 (powered from voltage source 72) is connected to a counter 111 which, each time it counts a preset number of marks (equal to the ratio of the step size of the numerical integration, explained below, to the separation of the optional marks 38), sends a signal by line 110 to I/O address port 112 whose output provides an address to memory (storage means) 114 each time a signal is received over line 110. The addresses are provided from microcomputer 113 through microcomputer interface (signal flow control circuitry) 115. Memory 114 is also connected to the output of A/D converter 61 so that a digital differential pressure value (i.e., localized density value) is stored in memory 114 (each time a signal is delivered on line 110), at the address delivered from I/O address port 112 to memory 114. In the computational circuitry at the measuring station, conventional signal conditioner 120 receives the signal from fluid sensor 62 over line 92 and delivers a conditioned fluid signal through interface 115 to microcomputer 113 to indicate when probe 20 is no longer immersed in the fluid being measured. Nor gate 122 (controlled from microcomputer 113) selectably gates the signal from conductivity probe 64 through signal conditioner 124 to microcomputer 113 to indicate when probe 20 is in water rather than in oil.

Microcomputer 113 can read stored data from memory 114 through interface 115 from addresses determined by the I/O address port 112.

Memory 114 also contains values for the areas enclosed by the tank at successive evenly-spaced levels above the bottom (which levels are separated by the same interval as the separation between levels in the fluid at which pressure difference data are recorded). Microcomputer (arithmetic processing means) 113 (working through microcomputer interface 115) uses the pressure and area information stored in memory 114 and the known vertical interval between successive levels in the tank to calculate the mass of the oil in the tank, using the trapezoid rule of numerical integration:

$$M = \frac{\Delta y}{gD}\left[ \tfrac{1}{2}A_0\Delta P_o + \sum_{i=1}^{N-1} A_i\Delta P_i + \tfrac{1}{2}A_N\Delta P_N \right]$$

where $\Delta y$ is the integration step size, $A_i$ is the cross-sectional area of the container at a level i $\Delta y$ above the bottom of the tank, $\Delta P_i$ is the pressure difference between levels i $\Delta y + D/2$ and i $\Delta y - D/2$ above the bottom of the tank, D is the vertical separation of ports 66 of the pressure transducer, and g is the local acceleration of gravity, (approximately 9.81 m/sec$^2$). Note that $\Delta P_i/gD$ is the mean density in an interval of thickness D. Within a vertical distance D/2 of the boundaries of the fluid being measured, $\Delta P$ is extrapolated from adjacent values of $\Delta P$ measured entirely within the fluid being measured.

Operation

To measure the mass of oil in the tank, the cross-sectional areas A(h) are stored in memory 114. Probe 20 is lowered to the bottom of the tank, and the reel is rotated to draw the transducer up through the fluid. As the transducer rises, each time one of the marks on the tape passes optical mark sensor 29, memory 114 is triggered to store the digital differential pressure value from pressure transducer 60. If water (which has a higher conductivity than oil) is encountered at any level, the conductivity signal informs the microcomputer, which then ceases the storage of pressure values until oil is again encountered. When the probe reaches the surface of the oil, fluid sensor 62 being no longer immersed, informs the microcomputer which then ceases the storage of pressure values. The microcomputer performs the calculation of the equation set forth above. The total mass is then displayed on conventional display elements 26 (FIG. 2). No temperature measurements are required.

Other Embodiments

Other embodiments are within the following claims. E.g., the tank may be a vessel or well or any other container; the pressure transducer need not be of the differential type in which case the pressure differences can be calculated at the measuring station; LED 52 and phototransister 54 can be replaced by a Hall effect switch, and marks 38 can be magnetic so that the Hall effect switch "reads" the marks as tape 22 moves; optical sensor 29 can be replaced by an encoding shaft and wheel (e.g., 4" circumference) on reel 24, whose angular position can be read continuously to indicate the corresponding vertical location of the transducer and the microcomputer can calculate the mass by continuous integration of the pressure difference function times a stored area function over the entire depth of the fluid; the oil may instead be any liquid or powder; the microcomputer can calculate the areas at each level from information about the container shape, rather than storing individual areas in advance; the microcomputer can be physically separated from the measuring station, so that the pressure data is first stored in the memory and later used to calculate the mass; and different area data for different tanks can be stored on different interchangeable memory elements so that the same measurement device can be easily used with different tanks.

We claim:

1. Apparatus for measuring the total mass of a fluid in a container, comprising
   pressure responsive, density determination means adapted to determine the localized density of said fluid to be measured as a function of pressure differential between two closely spaced, vertically separated measuring points in the fluid,
   means enabling said density determination means to determine the localized density values throughout the depth of said fluid,
   storage means for storing predetermined horizontal cross-sectional area values of the container as a function of depth, and
   computational circuitry responsive to the density determination means and the storage means for providing a total mass signal corresponding to an integral, over the depth of the fluid, of products of localized density values times the corresponding area values.

2. The apparatus of claim 1 wherein said density determination means includes a vertically movable pressure transducer and said means enabling determination of density values throughout the fluid depth includes
   traverse means for moving the transducer throughout the depth of the fluid, and a level indicator for providing values indicative of the vertical location of the transducer in the fluid with respect to each of its pressure readings.

3. The apparatus of claim 2 wherein
   said pressure transducer comprises two pressure sensors at two vertically spaced-apart positions and is arranged to provide signals corresponding to the difference in pressures at the two positions, said signals being indicative of the mean localized density of the fluid between the two positions.

4. The apparatus of claim 3 adapted for use with fluids whose density varies with temperature variations over the depth of the fluid and wherein
   said computational circuitry adapted to determine said integral in steps each corresponding to a finite interval of depth, and
   said finite interval and the vertical distance between said spaced-apart positions of said pressure sensors being selected to be small compared with the magnitude of variations, over the depth of the fluid, of the cross-sectional area and the density of the fluid.

5. The apparatus of claim 1 adapted for use wherein the container holds an additional fluid vertically separate from the fluid to be measured, said additional fluid having an electrical conductivity different from the fluid to be measured, and wherein the apparatus includes an element sensitive to electrical conductivity, said apparatus responsive to said element to exclude the mass of the additional fluid from the total mass signal.

6. The apparatus of claim 5 wherein the computational circuitry is adapted, on the basis of differences in electrical conductivity, to measure oil, and to exclude water.

7. The apparatus of claim 1 wherein the storage means is adapted to store the cross-sectional area values for different containers having respectively different geometric configurations.

8. The apparatus of claim 1 wherein said storage means is adapted to store said localized density values.

9. The apparatus of claim 1 wherein said computational circuitry comprises
   programmable arithmetic processing means for computing said total mass signal, and
   signal flow control circuitry connected to route said localized density signals and said stored cross-sectional area values to said arithmetic processing means.

10. The apparatus of claim 9 wherein
    said computational circuitry further comprises fluid sensing means for delivering immersion signals indicative of when said density determination means is not immersed within said fluid,
    said signal flow control circuitry is adapted to route said immersion signals to said arithmetic processing means, and
    said arithmetic processing means is arranged to limit said total mass signal computation to positions at which said density determination means is immersed in said fluid.

11. The apparatus of claim 10 wherein the container holds an additional fluid vertically separate from the fluid to be measured, said additional fluid having an electrical conductivity different from the fluid to be measured, and wherein the apparatus includes an element sensitive to the electrical conductivity of the fluid in which said density determination means is immersed, said signal flow control circuitry is connected to route signals from said element to said arithmetic processing means, and said arithmetic processing is arranged to limit said total mass signal computation to positions at which said density determination means is immersed in the fluid to be measured.

* * * * *